(12) United States Patent  
Mathiasson

(10) Patent No.: US 9,457,155 B2  
(45) Date of Patent: Oct. 4, 2016

(54) PROTECTIVE COVER FOR DISPOSABLE INJECTION NEEDLES

(71) Applicant: Laponia Innovatio AB, Gällivare (SE)

(72) Inventor: Margaretha Mathiasson, Gällivare (SE)

(73) Assignee: Laponia Innovatio AB, Gällivare (SE)

( * ) Notice: Subject to any disclaimer, the term of this patent is extended or adjusted under 35 U.S.C. 154(b) by 0 days.

(21) Appl. No.: 14/411,334

(22) PCT Filed: Jun. 14, 2013

(86) PCT No.: PCT/SE2013/050699  
§ 371 (c)(1),  
(2) Date: Dec. 24, 2014

(87) PCT Pub. No.: WO2014/003632  
PCT Pub. Date: Jan. 3, 2014

(65) Prior Publication Data  
US 2015/0335828 A1 Nov. 26, 2015

(30) Foreign Application Priority Data  
Jun. 29, 2012 (SE) ...................... 1250737

(51) Int. Cl.  
*A61M 5/32* (2006.01)

(52) U.S. Cl.  
CPC ......... *A61M 5/3204* (2013.01); *A61M 5/3216* (2013.01); *A61M 5/3293* (2013.01); *A61M 2005/3217* (2013.01); *A61M 2005/3284* (2013.01); *A61M 2207/00* (2013.01)

(58) Field of Classification Search  
CPC ........... A61M 5/3204; A61M 5/3216; A61M 5/3293; A61M 2005/3217; A61M 2005/3284; A61M 2207/00  
See application file for complete search history.

(56) References Cited

U.S. PATENT DOCUMENTS

| | | | |
|---|---|---|---|
| 5,002,533 A | 3/1991 | Jullien | |
| 5,066,279 A | 11/1991 | Russell | |
| 5,135,509 A | 8/1992 | Olliffe | |
| 5,158,550 A | 10/1992 | Scholl, Jr. | |
| 5,188,600 A | 2/1993 | Jullien | |
| 5,188,611 A | 2/1993 | Orgain | |
| 5,662,617 A * | 9/1997 | Odell | A61M 5/3216 128/919 |
| 5,776,076 A | 7/1998 | Chen | |
| 2003/0028150 A1 | 2/2003 | Tuen | |
| 2008/0154192 A1 | 6/2008 | Schraga | |
| 2010/0198152 A1 | 8/2010 | Haindl et al. | |
| 2011/0319831 A1* | 12/2011 | Bode | A61B 5/1405 604/192 |

FOREIGN PATENT DOCUMENTS

| | | |
|---|---|---|
| EP | 0 832 660 A2 | 4/1998 |
| WO | WO 95/34335 A1 | 12/1995 |
| WO | WO 97/10016 A1 | 3/1997 |

\* cited by examiner

*Primary Examiner* — Emily Schmidt  
*Assistant Examiner* — Lauren M Peng  
(74) *Attorney, Agent, or Firm* — Blank Rome LLP

(57) ABSTRACT

A protective cover (4) to be used with disposable injection needles (1), such as those used for injection of insulin, which injection needles comprise a base (3) and a needle (2) fastened in the base, said protective cover comprising a hood (9) pivotably fastened on the base, said hood (9) being arranged to be pivotable, with the one and the same hand that holds a syringe on which the injection needle is arranged, between an inactive position at the side of the needle (2) of the injection needle and an active position in front of the needle (2) seen in the longitudinal direction of the needle.

5 Claims, 3 Drawing Sheets

PROTECTIVE COVER FOR DISPOSABLE INJECTION NEEDLES

TECHNICAL FIELD

The present invention relates to a protective cover for disposable injection needles, such as those being used with so called insulin pens.

BACKGROUND

In connection with injection needles such as those being used with insulin pens a base of an injection needle is screwed onto a syringe to be used for the injection of insulin. In the base there is a needle and on the needle there is a protective sleeve, which is removed before use. After use the protective sleeve is again threaded onto the needle. The sleeve is so very narrow, that it is easy to miss the needle with the accompanying risk for puncture wounds.

Another problem with the prior art solutions is that users re-use used injection needles several times. This implies a risk for infections but also tissue damages because of the fact that the needle loses its sharpness.

Accordingly, there is a need for improved protective covers for injection needles.

SUMMARY OF THE INVENTION

One object of the invention is to provide a protective cover for injection needles which eliminates or at least mitigates the risk of stitch or puncture damages.

A further object of the invention is to provide a protective cover for a needle which also makes it hard or even impossible to re-use a needle.

These and also other objects are attained with the protective needle cover according to the invention having the characterizing features according to claim 1. Developments and preferred embodiments are defined in the sub claims.

By way of the construction of the protective needle cover it is accomplished that when the needle has been used once, a hood is made to cover the point of the needle by raising up the hood in front of the needle, said hood automatically being locked in a raised position, while at the same time the needle is deformed by the hood when the hood is raised.

One advantage with the invention is that the raising up of the hood can be done with the one and the same hand that holds the syringe, and no part of the hand has to pass the area of the needle tip when it is not covered by the hood.

SHORT DESCRIPTION OF THE DRAWINGS

Figure 1:
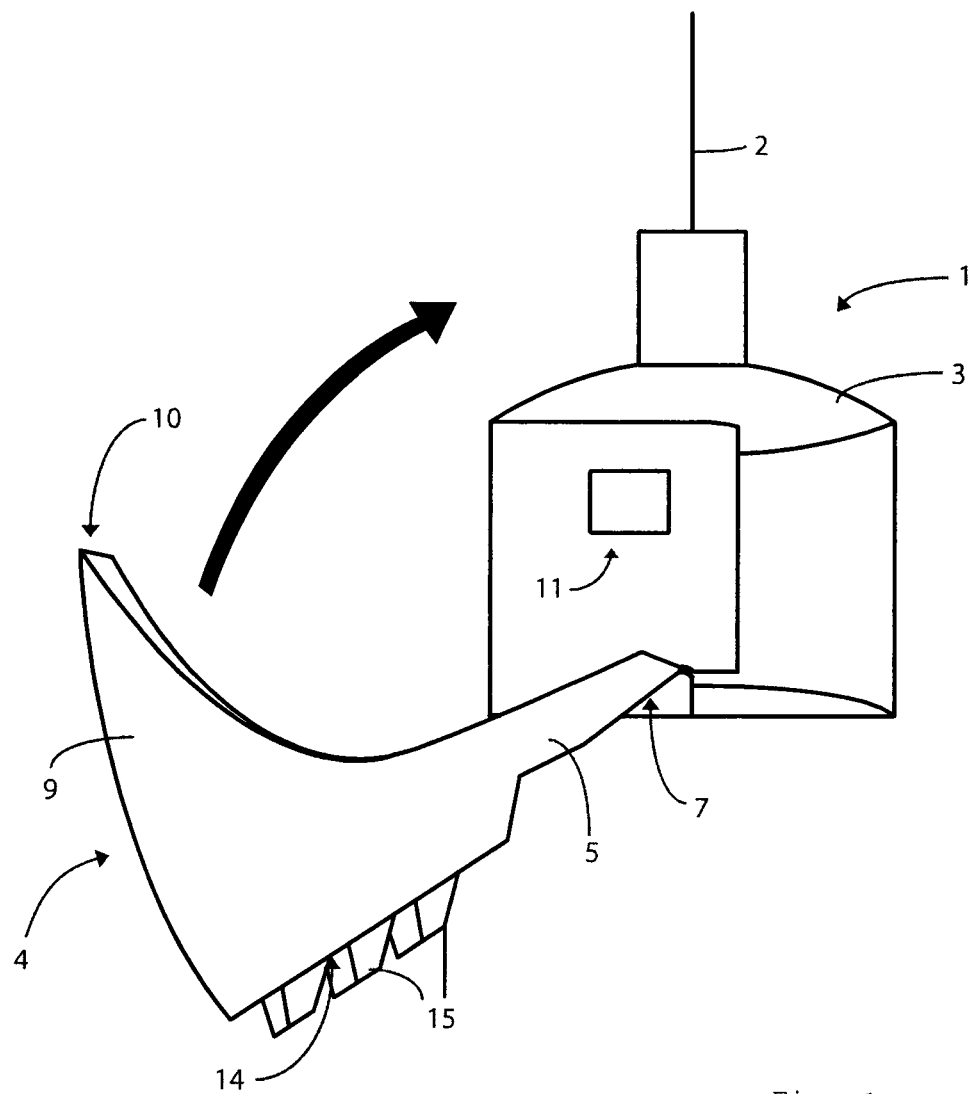
Figure 2:
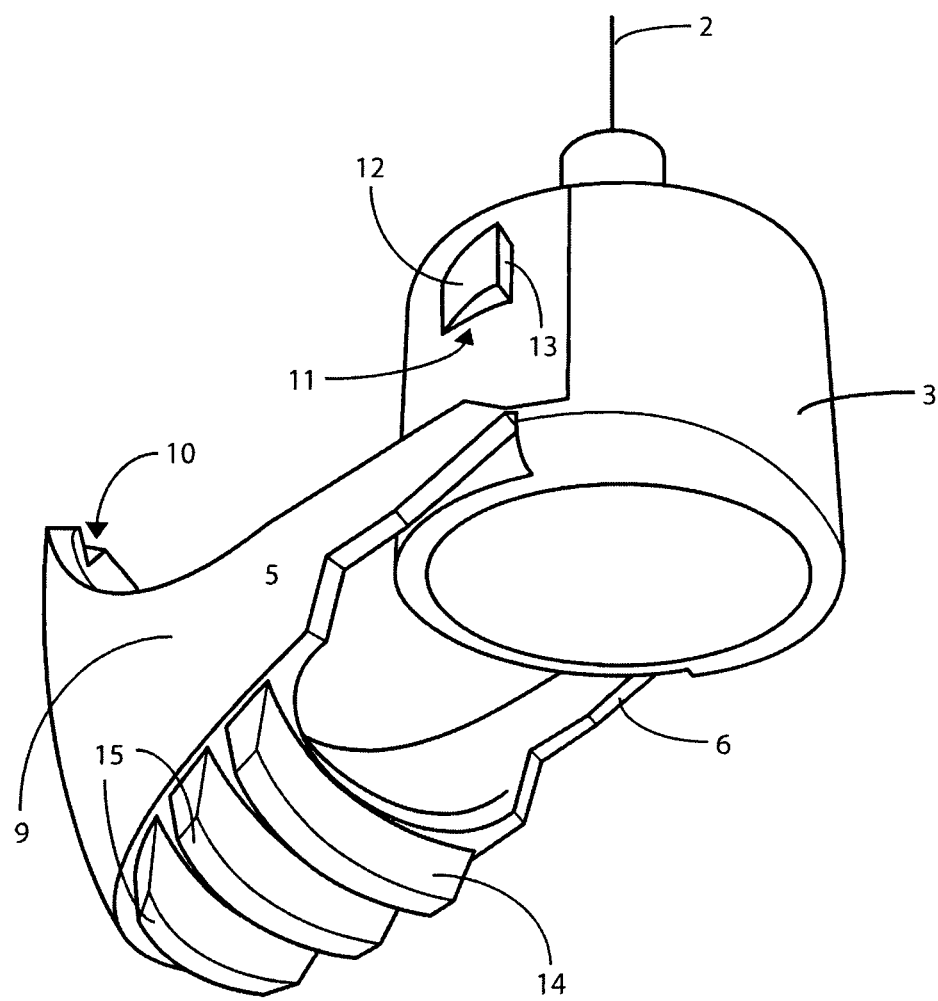
Figure 3:
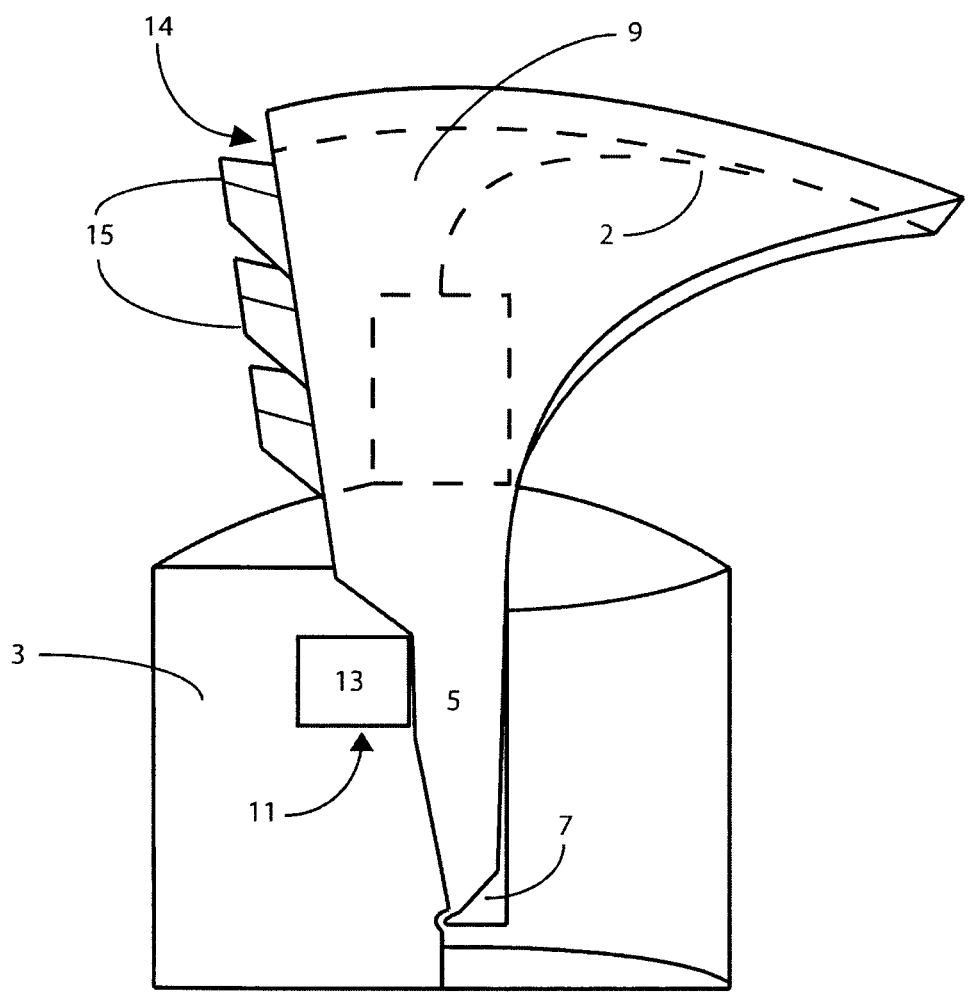

The invention will now be described in detail in the following detailed description with reference to one embodiment of the invention illustrated in the drawings, on which FIG. 1 schematically shows a injection needle with a protective needle cover according to the invention manufactured in one piece with a needle base with needle, in an inactive position;

FIG. 2 shows the means according to FIG. 1 in a perspective view obliquely from below, also in an inactive position; and FIG. 3 schematically shows the base with activated protective needle cover.

DETAILED DESCRIPTION OF THE INVENTION

Accordingly, the present invention relates to a means that protects against puncture wounds when used with disposable injection needles. The injection needles might be part of a disposable syringe or could be separate and designed to be fastened on the end of a syringe, such as by a threaded connection, or locking by form or force, e.g. with the aid of grooves.

According to today's practice injection needles are delivered with a protective needle cover in the form of a sleeve threaded onto the needle. Often this protective needle cover is threaded onto the needle again after use of the needle, and it is e.g. then, among several other occasions, that puncture damages might occur. This sleeve-like protective needle cover can still be used for injection needles in combination with the protective needle cover according to the present invention until an injection is to be delivered.

In FIG. 1 is shown in a very schematic view an injection needle with a protective needle cover according to the invention. The injection needle is referenced 1, and comprises a needle 2 and a base 3. A protective needle cover 4 is according to the invention pivotably connected to the base 3.

According to a preferred embodiment of the invention the base is manufactured in one piece with the protective needle cover 4 by injection molding using a suitable plastic material. The protective needle cover comprises a yoke having two arms 5, 6, which are pivotably attached to the base, and according to the preferred embodiment are via hinges 7,8 of plastic material arranged in one piece with the rest of the parts constituting the device. The arms 5, 6 of the yoke transition into a hood 9 at the ends lying opposite to the hinges.

The hood 9 might be domed, as is shown in the drawings and can have, as is also shown in the drawings, curved side edges to make it possible to swing it up over the base and the needle arranged therein, at a height over the base being lower than the protrusion of the needle beyond the base. The hood might then have a guiding groove or a notch 10 at a front edge in order to catch the needle when raising the protective needle cover according to the invention.

In FIG. 2 the protective needle cover is shown schematically seen obliquely from below in order to illustrate the suspension of the protective needle cover in the base 2 of the injection needle. The two arms 5, 6 are hingedly connected to the base on diametrically opposite sides thereof.

For reasons related to the manufacture but also for economical reasons the base is preferably manufactured integrally with the protective needle cover from a suitable plastic material. This is however not of a fundamental importance for the function of the invention, but instead the pivotability can be obtained also in other ways, if desirable for some reason. For example, the arms can be provided with pins which can be snapped into corresponding apertures in the base, or in any other suitable way.

On the base, shoulders 11 are arranged, said shoulders having a first ramp-like inclined side 12, which acts as a straight for the respective arms of the protective needle cover, and a second side 13, which runs perpendicular to the base. Thereby a shoulder is formed, on which the arms can slide when raising the protective needle cover, and in the upraised position the arms snap in automatically behind the shoulders, and cannot be released without further effort from that position, which is illustrated in FIG. 3.

After all, it is of course possible to remove the hood from the base. In order to as far as possible prevent re-use of an injection needle, the length of the arms 5, 6 is according to a preferred embodiment of the invention adapted so that the needle 2 will be deformed, i.e. curved/bent, as is indicated with broken lines in FIG. 3, to such an extent that it becomes useless.

In the embodiment shown in the drawings the protective needle cover 4 has a backside 14 which extends substantially in parallel with the pivot arms 5, 6, but only partly covers the interspace between the arms in order not to obstruct the raising of the protective needle cover over the base. Further, the backside has protrusions 15 which enhance the grip during operation. With this embodiment the protective needle cover can without any risk be handled with the one and the same hand that holds the syringe, and when raising the hood the hand never has to be on the "wrong" side of the needle point, and a safe handling can be guaranteed.

Of course it is possible to vary the detailed construction of the protective needle cover within the scope of the following claims. Thus, instead of the locking shoulders on the base, the hood could be provided on the inside with a snap ring fastener, which snaps onto the base surrounding the needle.

Further, it is possible to provide the hood with a shoulder on the inside, designed so that when the hood meets the needle and bends it during the raising, the point of the needle ends up behind this shoulder, and thereby re-use of the needle is made even more difficult.

The invention claimed is:

1. A protective cover to be used with disposable injection needles, such as those used for injection of insulin, which injection needles comprise a base and a needle fastened in the base, said protective cover comprising a domed hood pivotably fastened on the base, said domed hood being arranged to be pivotable, with the one and the same hand that holds a syringe on which the injection needle is arranged, between an inactive position at the side of the needle of the injection needle and an active position in front of the needle, seen in the longitudinal direction of the needle, wherein the domed hood has the form of a yoke having two arms, which at one end carry the domed hood and at their opposite ends are pivotably connected to the base of the injection needle, and wherein the length of the arms is so dimensioned that when bringing the domed hood to its active position, a height of the domed hood is lower than a protrusion of the needle from the base, such that the needle is curved/bent to such an extent that it becomes useless while at the same time the extension of the domed hood is such that the needle is completely covered by the domed hood.

2. The protective cover according to claim 1, wherein the domed hood is manufactured in one piece with the base of the injection needle, whereby the pivotability is achieved by the domed hood being connected to the base via integral bridges of material.

3. The protective cover according to claim 1, wherein the domed hood is arranged to be locked irreversibly in the active position.

4. The protective cover according to claim 1, wherein the domed hood in the active position is locked with the aid of two locking shoulders arranged on the base.

5. The protective cover according to claim 4, wherein the shoulders have a straight inclined as a ramp, on which the arms of the yoke can slide up when raising the domed hood from the inactive position to the active position, and with one side standing perpendicularly out from the base, against which side the respective arm of the yoke rests when the domed hood is in the active position in which it covers the needle.

* * * * *